(12) United States Patent
Mirsky

(10) Patent No.: US 6,416,794 B1
(45) Date of Patent: Jul. 9, 2002

(54) METHODS AND COMPOSITIONS FOR TREATING CATARACTS USING SUBSTANCES DERIVED FROM YEAST OR SALTBUSH

(75) Inventor: Nitsa Mirsky, Nofit (IL)

(73) Assignee: Natural Compounds Ltd., Tivon (IL)

( * ) Notice: Subject to any disclaimer, the term of this patent is extended or adjusted under 35 U.S.C. 154(b) by 0 days.

(21) Appl. No.: 09/617,865

(22) Filed: Jul. 17, 2000

Related U.S. Application Data

(63) Continuation-in-part of application No. 09/395,534, filed on Sep. 14, 1999, now Pat. No. 6,261,606.

(51) Int. Cl.⁷ .......................... A01N 65/00; A61K 35/78
(52) U.S. Cl. ......................................... 424/725; 424/779
(58) Field of Search .................... 426/195.1, 195.16, 426/195.15, 725, 779

(56) References Cited

U.S. PATENT DOCUMENTS 5,075,116 A    12/1991  LaHaye et al. ............. 424/617
5,804,597 A    9/1998   Yamakoshi et al. ......... 514/456

OTHER PUBLICATIONS

Thornber et al. Protection Against Sucrose–Induced Retinal Capillary Damage in the Wistar Rat; Journal of Nutrition 114/6, pp. 1070–1075, 1984.*
Jarrett R.J. et al., 1982, Diabetologia 22:79–84.
Jeejebhoy K.H. et al., 1977, Am J Clin Nutr, 30:531–38.
Anderson R.A. and Mertz W., 1977, Trends in Biochem. Sci. 2, 277–79.
Evans GW et al., 1973, Biochem Biophys Res Commun 50:718–22.
Schmidt–Nielsen K et al., 1964, Science 143: 689–690.
Sivak JG et al., 1986, Vision Res 26 (11): 1873–1879.

* cited by examiner

*Primary Examiner*—Jon P. Weber
*Assistant Examiner*—Patricia D Patten
(74) *Attorney, Agent, or Firm*—Rashida A. Karmali

(57) ABSTRACT

Compositions and methods having anticataract and antiretinopathy activity, comprising compounds extracted from natural resources including yeast and Saltbush or synthetic chromium complexes, for the prevention or treatment of cataracts and retinopathy.

8 Claims, 17 Drawing Sheets

Control, 96 hrs

Control, 13 days 450 mg% glucose, 13 days 450 mg% glucose and GTF, 48 hrs

Rat eyes – healthy, diabetic and diabetic treated with GTF

*a) Healthy*

*b) Diabetic*

*c) Diabetic + GTF*

*d) Diabetic + GTF*

METHODS AND COMPOSITIONS FOR TREATING CATARACTS USING SUBSTANCES DERIVED FROM YEAST OR SALTBUSH

CROSS-REFERENCE TO OTHER APPLICATIONS

This is a Continuation-in-Part of application Ser. No. 09/395,534 filed Sep. 14, 1999, now issued as U.S. Pat. No. 6,261,606B1 on Jul. 17, 2001, which reference is incorporated herein in its entirety.

FIELD OF THE INVENTION

The present invention relates to compositions and methods for the prevention and treatment of cataracts and retinopathy. Specifically, the present invention relates to selected compositions with or without chromium containing compounds, isolated from a variety of natural sources, including, but not limited to, a yeast strain *S. carlsbergensis, S. Cerevisiae* or any commercial source of yeast extract; and from the Saltbush, *Ariplex halimus*, growing in the Negev Desert near the Dead Sea and other arid and semiarid areas in the middle east, for the prevention or treatment of cataracts and retinopathy. Additionally, the present invention relates to formulations of synthetic sources of chromium complexes alone or in combination with compositions extracted from natural sources, for the prevention and treatment of cataracts and retinopathy.

1. BACKGROUND OF THE INVENTION

Cataract excision is the most common type of operation in the aged population. Cataract is the cause of fifty percent of the blindness in the world and about one million cataract procedures are performed in the United States alone. Macular degeneration associated with aging is now a major cause of blindness. The crystalline lens loses its normal transparency and, as a result, there is interference with the passage of light through the lens. As the lens become opacified, vision is disturbed depending on the degree of opacification.

There are different etiologies for cataract formation such as aging, congenital lesions or trauma, some medicines such as steroids and glaucoma medications, cigarettes, alcohol, as well as inborn metabolic errors such as galactosemia, and diseases like diabetes.

At present, pirenoxine drops, proanthocyanidin drops, reduced glutathione drops, salivary gland hormone tablets, vitamin and mineral compositions and the like are used clinically for cataracts. U.S. Pat. No. 5,075,116 issued Dec. 24, 1991, U.S. Pat. No. 5,804,597 issued Sep. 8, 1998 and Machlin, L. et al., 1987, *FASEB J*. 1:441–445. However, these medications do not produce an effective therapeutic response and the only currently available treatment for cataracts is surgery.

2. SUMMARY OF INVENTION

The present invention relates to methods and compositions for the prevention and treatment of cataracts and retinopathy, comprising materials isolated from natural sources, including, but not limited to, a yeast strain-*S. carlsbergensis, S. cerevisiae* or any commercial source of yeast; or yeast extract or the Saltbush-*Ariplex halimus*, growing in the Negev Desert near the Dead Sea and other arid and semiarid areas in the middle east.

The present invention also provides methods and compositions of synthetic sources of chromium complexes including, but not limited to, chromium gluconate, chromium sulfate, chromium cysteine, chromium-N-acetyl cysteine, chromium glutathione, chromium acetate, chromium citrate, chromium ascorbate or chromium tartarate, for the prevention and treatment of cataracts and retinopathy.

The present invention provides methods and formulations having hypoglycemic and/or hypolipidemic activity, containing natural or synthetic compositions with or without chromium, exhibiting Glucose Tolerance Factor (GTF) activity, for prevention and treatment of cataracts and retinopathy.

The present invention provides methods and formulations having antioxidant activity, containing natural and synthetic compositions with or without chromium, exhibiting free radical scavenging activity, for prevention and treatment of cataracts and retinopathy.

According to the present invention, the methods and compositions comprise materials isolated from natural sources, synthetic chromium complexes, GTF, given alone or in combination with any one or more of the agents, for the prevention and treatment of cataracts and retinopathy.

The present invention provides formulations containing natural and synthetic complexes with or without chromium, which can be applied in combination with an effective amount of one or more additional antioxidants including vitamin C, vitamin E, reduced glutathione, manganese, beta-carotene, ergothioneine, zinc, selenium, cysteine, N-acetyl cysteine, methionine or 2-mercaptoethanol.

According to an additional aspect of the present invention, there is provided a method to prevent and treat cataracts and retinopathy by applying formulations having an effective amount of anticataract-antiretinopathy compositions with or without chromium, isolated from natural sources or containing synthetic chromium complexes.

According to yet another aspect of the invention; there is provided a method to prevent and treat cataracts and retinopathy by applying formulations with or without chromium isolated from natural sources and/or containing synthetic chromium complexes in combination with an effective amount of one or more antioxidants including vitamin C, vitamin E, reduced glutathione, manganese, beta-carotene, ergothioneine, zinc, selenium, cysteine, N-acetyl cysteine, methionine or 2-mercaptoethanol.

Still other objects and advantages of the invention will in part be obvious and will in part be approved from the specification.

The invention accordingly comprises the several steps and the relations of one or more of such steps with respect to each of the others, and the product embodying properties, which are adapted to effect such steps and methods, all as exemplified in the following detailed disclosure, and the scope of the invention will be indicated in the claims.

3. BRIEF DESCRIPTION OF THE DRAWINGS

For a fuller understanding of the invention, reference is had to the following description taken in connection with the accompanying drawings, in which:

FIG. 1 is a computer printout of the Focal length profile for a control bovine lens 24 hours in organ culture. Abscissa indicates focal length (mm). Ordinate refers to laser beam distance (mm) from the optical center (0.0) of the lens. The plus signs (+) indicate the focal points for each incident beam position away from the optic axis. The array of 22 lines coming to a focal point represents the direction of the refracted beams for each of the 22 incident beam positions.

FIG. 2 is a computer printout of the Focal length profile for a control bovine lens 48 hours in organ culture. Abscissa indicates focal length (mm). Ordinate refers to laser beam distance (mm) from the optical center (0.0) of the lens. The plus signs (+) indicate the focal points for each incident beam position away from the optic axis. The array of 22 lines coming to a focal point represents the direction of the refracted beams for each of the 22 incident beam positions.

FIG. 3 is a computer printout of the Focal length profile for a control bovine lens 72 hours in organ culture. Abscissa indicates focal length (mm). Ordinate refers to laser beam distance (mm) from the optical center (0.0) of the lens. The plus signs (+) indicate the focal points for each incident beam position away from the optic axis. The array of 22 lines coming to a focal point represents the direction of the refracted beams for each of the 22 incident beam positions.

FIG. 4 is a computer printout of the Focal length profile for a control bovine lens 96 hours in organ culture. Abscissa indicates focal length (mm). Ordinate refers to laser beam distance (mm) from the optical center (0.0) of the lens. The plus signs (+) indicate the focal points for each incident beam position away from the optic axis. The array of 22 lines coming to a focal point represents the direction of the refracted beams for each of the 22 incident beam positions.

FIG. 5 is a computer printout of the Focal length profile for a control bovine lens 13 days in organ culture. Abscissa indicates focal length (mm). Ordinate refers to laser beam distance (mm) from the optical center (0.0) of the lens. The plus signs (+) indicate the focal points for each incident beam position away from the optic axis. The array of 22 lines coming to a focal point represents the direction of the refracted beams for each of the 22 incident beam positions.

Figure 13:
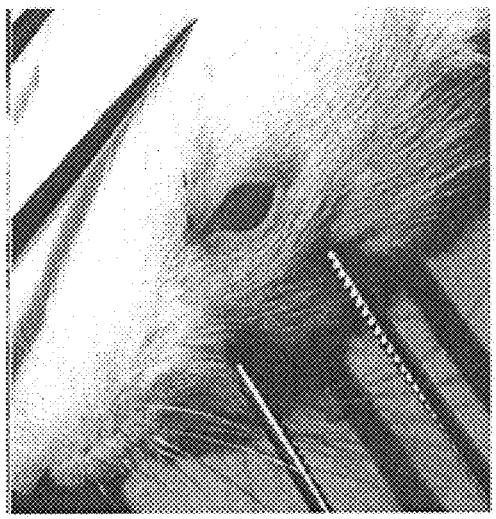
Figure 13:
Figure 13:
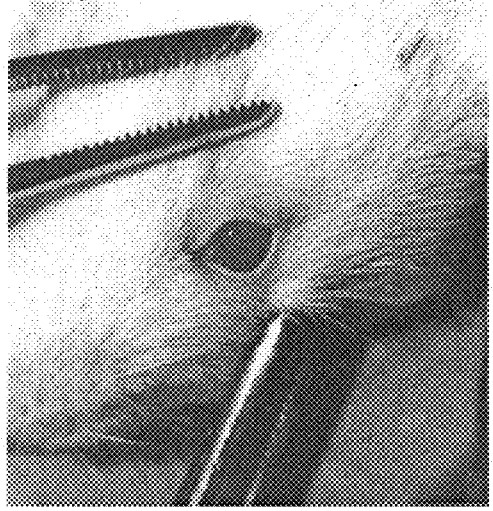
Figure 13:

FIG. 13 describes rats' eyes from healthy (a), diabetic (b) or diabetic treated with 15 oral doses of GTF (280 ng Cr/rat) (c,d). Note the decrease in turbidity of lens of animals treated with GTF compared to untreated lens (a), where a severe cataract can be seen.

Figure 14:
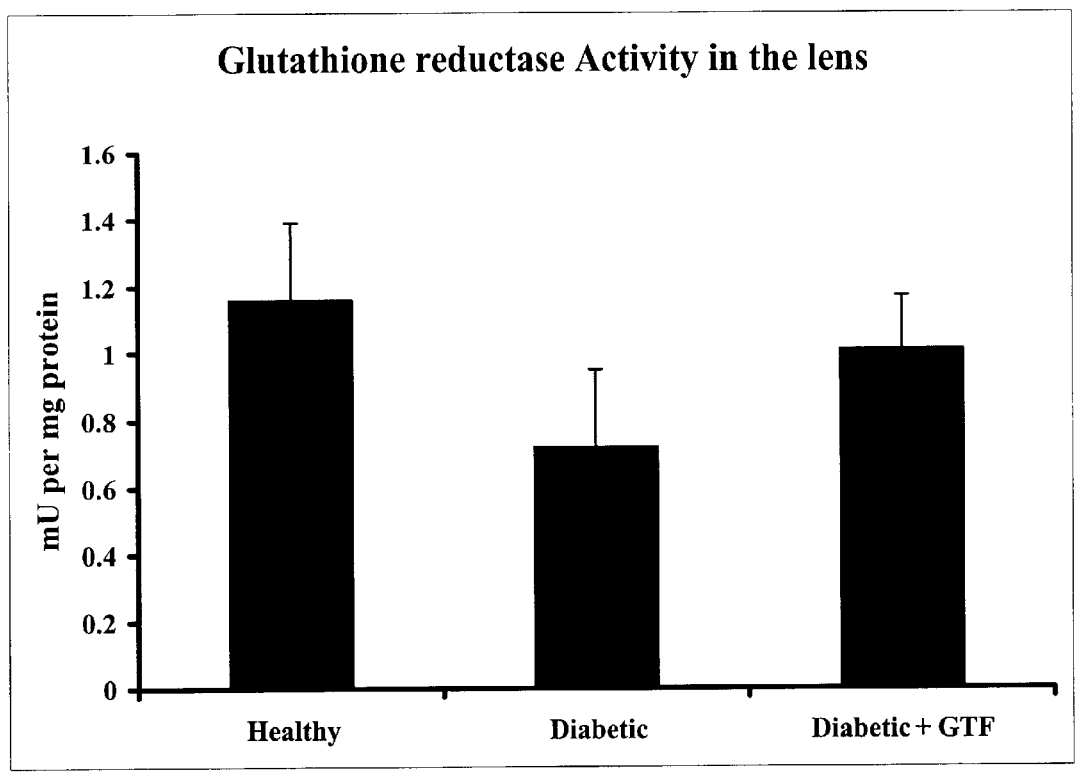

FIG. 14 illustrates glutathione reductase activity in healthy control rat lenses, in diabetic lenses and lenses excised from diabetic animals treated with 5 oral doses of GTF (560 ng Cr/dose).

Figure 15:
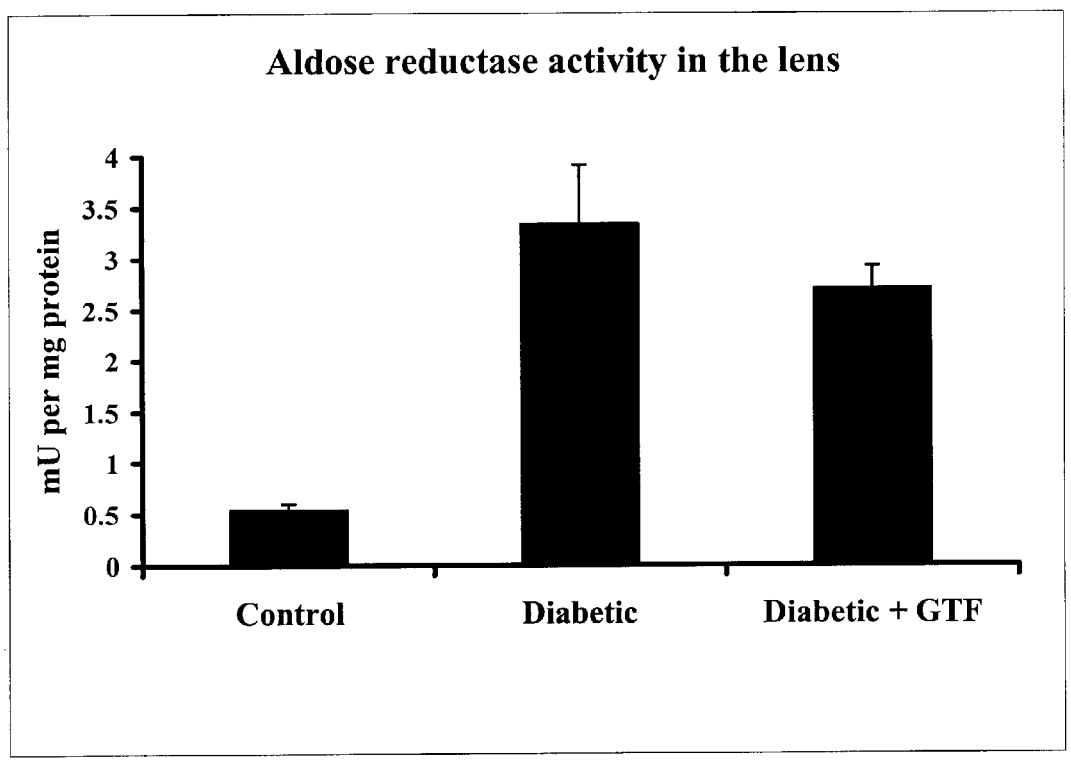

FIG. 15 illustrates Aldose reductase activity in healthy control rat lenses, in diabetic lenses and lenses excised from diabetic animals treated with 5 oral doses of GTF (560 ng Cr/dose).

Figure 16:
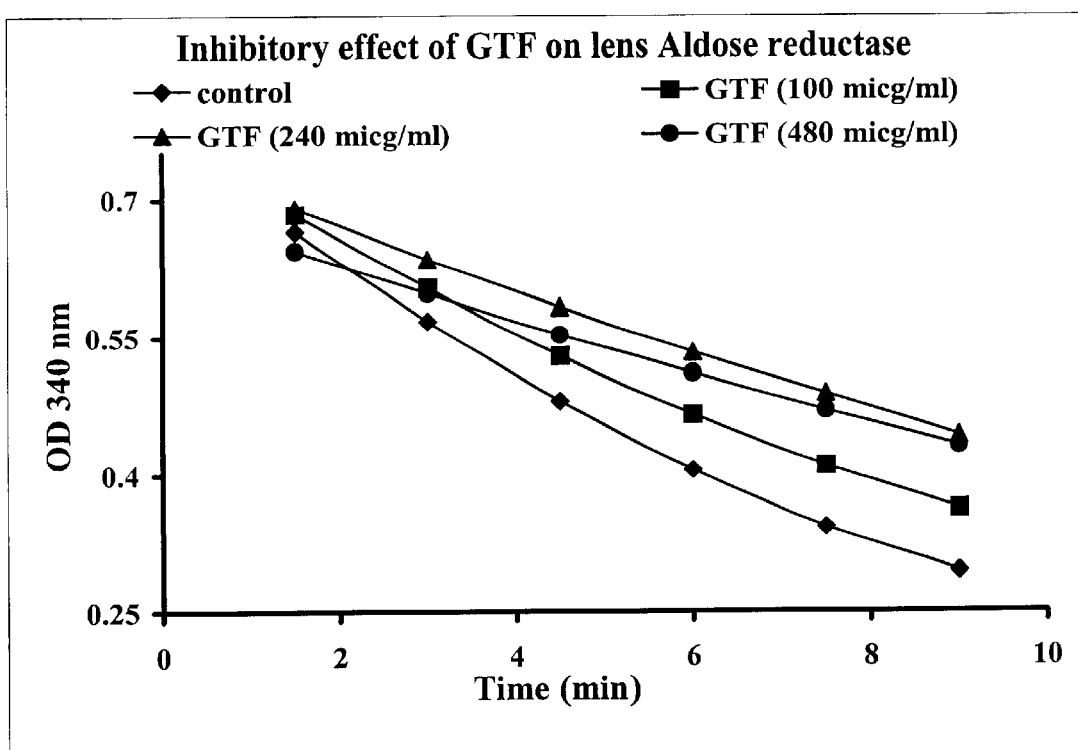

FIG. 16 illustrates dose response inhibition of lens Aldose reductase actitvity in vitro by an active fraction isolated from yeast (GTF).

Figure 17:
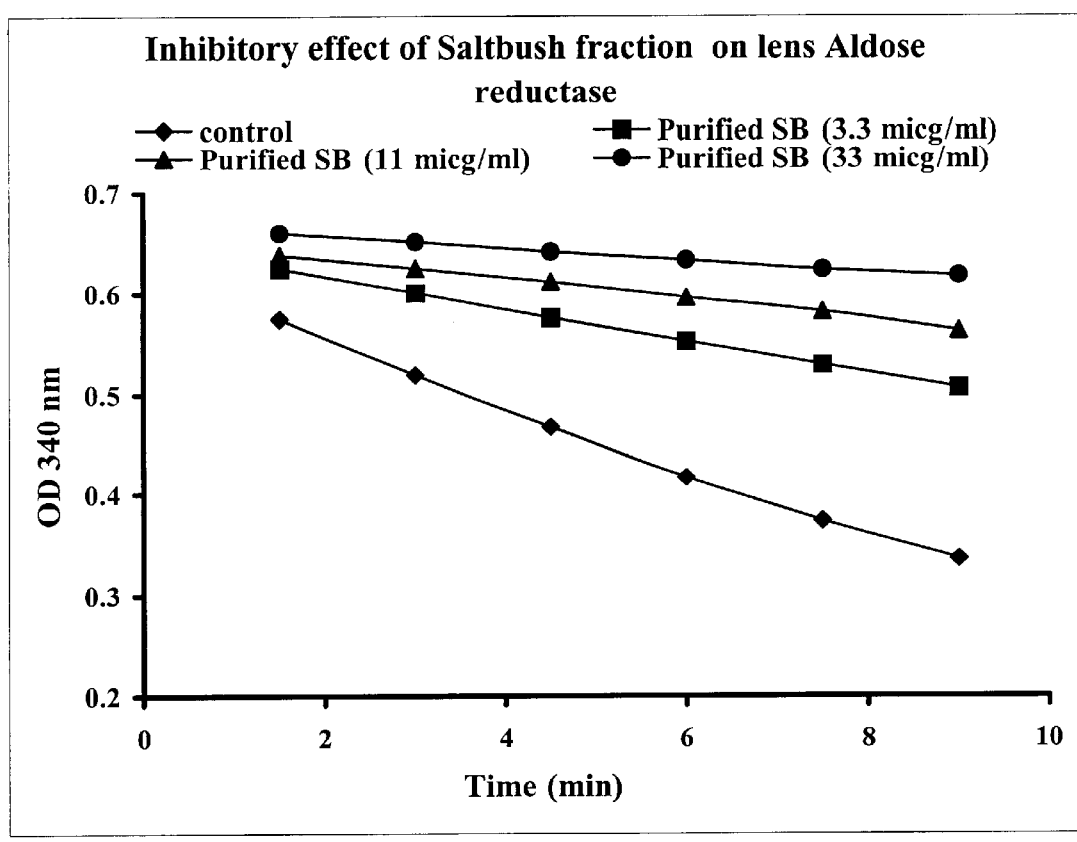

FIG. 17 illustrates dose response inhibition of lens Aldose reductase actitvity in vitro by an active fraction isolated from the Saltbush (ACMS).

4. DETAILED DESCRIPTION OF THE INVENTION

The present invention provides methods and compositions for the prevention and/or treatment of cataracts and retinopathy, and comprising anticataract-antiretinopathy materials isolated from a variety of natural sources or synthetic chromium complexes. The natural sources include, but are not limited to, a yeast strain *S. carlsbergensis, S. Cerevisiae* or any commercial source of yeast extract; or Saltbush *Ariplex halimus*, growing in the Negev Desert near the Dead Sea or other areas in the middle east. The synthetic chromium complexes include, but are not limited to, chromium gluconate, chromium sulfate, chromium cysteine, chromium-N-acetyl cysteine, chromium glutathione, chromium acetate, chromium citrate, chromium ascorbate or chromium tartarate.

The methods are directed to the use of anticataract-antiretinopathy compositions described above, in the prevention and treatment of cataracts and retinopathy. Further, various mixtures of the anticataract-antiretinopathy compositions with or without other mixtures of antioxidants are included. These materials and methods of use in the prevention and/or treatment of cataracts and retinopathy are included in the present invention and the methods of preparations of these materials are described in the pending applications, Ser. No. 09/395,534, which are incorporated herein by reference in their entirety.

There are different etiologies for cataracts and retinopathy, including those related to aging (senile cataracts) or those related to diabetes, congenital lesions, trauma or medicines.

4.1 Senile Cataracts

Age-related cataracts consist of any cataracts without a known cause that develop in the elderly people. Clinically, age-related cortical cataracts include three main types: in the peripheral cortex, in the cortex next to the nucleus, and in the posterior cortex of the lens. The nuclear cataract is the acceleration of the normal densification process of the innermost lens fibers. Oxidative mechanisms are causally linked to cataract formation. According to the present invention, the methods and compositions are directed to scavenge free radicals and retard progression of cataracts and macular degeneration.

4.2 Diabetic Cataracts or Retinopathy.

Diabetes substantially increases the probability of cataract formation in the age group from 40 to 49, and approximately doubles or triples this probability for the age group 50 to 69. Ederer F. et al., 1981, *Am J. Ophthalmol.* 91: 381–395. Diabetes mellitus is regarded as the third prevalent disease in the western world. Diabetes mellitus is a complex syndrome involving severe insulin dysfunction in conjunction with gross abnormalities in glucose homeostasis and lipid metabolism. The disease is generally divided into 2 major subgroups. One group is insulin-dependent diabetes mellitus (IDDM), which has also been referred to as 'juvenile-onset diabetes,' or Type 1 diabetes. The second group is referred to as non insulin-dependent diabetes mellitus (NIDDM), which is also termed 'maturity-onset diabetes' or Type II diabetes. In the former variety of the disease there is total or near total loss of insulin secretion from the islets of Langerhans in the pancreas, resulting in enhancement of gluconeogenesis, elevated blood glucose levels and gross loss of muscle and fat. In the latter type of diabetes, insulin secretion is low or tardy so that blood glucose levels rise in to the hyperglycemic range (10 mM versus 5 mM for normals). IDDM is most evident in the young whereas NIDDM is strongly age-related. Both forms are equally devastating with respect to their later complications. The individual with diabetes has a 25-fold increase in the risk of blindness, a 20-fold increase in the risk of renal failure, a 20-fold increase in the risk of amputation as a result of gangrene and a 2- to 6-fold increased risk of coronary hear disease and ischemic brain damage. Almost half of those diagnosed as diabetic before age 31 die before they reach 50, largely as a result of cardiovascular or renal complications, often with many years debilitating disease beforehand. The financial burden upon the patient and society as a whole is enormous.

Two types of cataracts occur in the diabetic patients: subcapsular and senile. Subcapsular cataract occurs predominately in type 1 diabetics, may come on fairly rapidly, and has a significant correlation with the hyperglycemia of uncontrolled diabetes. This type of cataract has a flocculent or "snowflake" appearance and develops just below the lens capsule. Senile cataract represents a sclerotic change of the lens nucleus. It is by far the most common type of cataract found in either diabetic or non-diabetic adults and tends to occur at a younger age in diabetic patients, particularly when glycemic control is poor. Two separate abnormalities found in diabetic patients, both of which are related to elevated blood glucose levels, may contribute to the formation of cataracts: (1) glycosylation of the lens protein and (2) an excess of sorbitol, which is formed from the increased quantities of glucose found in the insulin-independent lens. Accumulation of sorbitol leads to osmotic changes in the lens that ultimately result in fibrosis and cataract formation.

In addition to the above abnormalities related to high glucose levels, oxidative stress is another major cause for diabetic cataracts. Oxidative insults like loss of lens glutathione, excessive $H_2O_2$, lipid peroxidation or lack of anti-oxidant enzymes are associated with cataract formation. Toxic metabolites of oxygen serve as initiators of lipid peroxidation and cataract formation. Bhuyan K. C. and Bhuyan D. K 1984. *Curr. Eye Res.* 3: 67–81. Hence, acceleration of oxidative processes, which occur in diabetes is expected to accelerate cataract formation, whereas enhancement of antioxidant capacity would be expected to retard or prevent cataract formation. GSH is probably the most important antioxidant in the lens. Lenticular GSH is dramatically decreased in diabetic animals Gonzales A. M. et al., 1983 *Diabetes* 32: 482–485 and diabetic humans Calvin H. I. C. et al. 1986, *Science 233: 553–555*. This decrease in GSH levels which likely renders the lens more susceptible to oxidative stress, could be one of the causes for the early onset of cataract in diabetic humans. Ederer F. et al., 1981 *Am J. Ophthalmol.* 91: 381–395. Most likely, GSH preserves the physicochemical equilibrium of lens proteins by maintaining high levels of reduced SH groups, oxidation of which results in alteration of protein linkages, their solubility and transparency (Calvin H. I. C. et al., 1986, *Science* 233: 553–555.

4.3 Biochemical Reactions in Cataractogenesis

These are several key enzymes present in the lens: Aldose reductase (AR) is induced by high glucose levels. This enzyme is involved in the formation of sorbitol from glucose. High activity of AR is related to cataractogenesis. Sorbitol, which can not pass through the lens membrane, accumulates in the lens leading to excess water entering into the lens, swelling and destruction of its fibers, and eventually increasing in turbidity and cataract formation. Other major enzymes in the lens epithelium are: glutathione reductase, hexokinase, aldolase, catalase, and glucose-6-phosphate dehydrogenase. Hexokinase and aldolase are the key enzymes of the glycolysis pathway. Catalase protects the cells from $H_2O_2$ accumulation, and glucose-6-phosphate dehydrogenase protects the cells against oxidation by providing reduced nicotinamide-adenine dinucleotide phosphate (NADPH) to the glutathione system, Glutathione reductase has also an important role in regenerating reduced glutathione in the lens, hus preventing lens protein oxidation and cross-linkage formation. Decrease in the activity of the above enzymes is associated with cataratogenesis.

4.4 Chromium Complexes and Glucose Tolerance Factor

Chromium (Cr) has been known for more than three decades as an essential trace element needed for animal and human nutrition. Schwarz K. Et al., 1959, 85:292–95. Rats fed a Cr-deficient diet developed glucose intolerance, in addition to elevated levels of blood glucose and cholesterol, decreased growth, and a reduced life span. Schroeder H. A., 1968, Am J Clin Nutr 21:230–44. Serum and tissue Cr concentrations in old or diabetic animals are lower than in young and healthy animals, Onkelinx C., 1977. Am J Physiol 232:E478–84. Chromium is the only element known in humans to decline in most organs with age. Its concentrations in people with diabetes are lower than in healthy adults. Guthrie E. In: Langard S, editor. *Biological and environmental aspects of chromium*. Amsterdam: Elsvier Biomedical Press; 1982 p 117–47.

Patients on long-term total parenteral nutrition developed severe symptoms of glucose intolerance, which could be partially reversed by intravenous administration of $CrCl_3$ of very high concentrations. Jeejebhoy K. H. et al., 1977, *Am J Clin Nutr*, 30: 531–38. Inorganic Cr compounds are poorly absorbed by the gut Donaldson R M et al. 1966, *J Lab Clin Med* 68: 484–93, whereas organic Cr compounds are well absorbed in the body.

The glucose tolerance factor (GTF) is a dietary agent that is required for normal glucose tolerance in animals and man. The earliest detectable symptom of GTF deficiency in animal, is and impairment of glucose tolerance, whereas more severe deficiency leads to glycosuria, fasting hyperglycemia, impaired growth, decreased longevity, elevated serum cholesterol, increased incidence of aortic plaques, and corneal opacities. Anderson R. A. and Mertz W., 1977, *Trends in Biochem. Sci.* 2, 277–279. GTF was first isolated as a partially purified preparation by Mertz and Schwarz, Schwarz K., Mertz W., 1959, *Arch Biochem Biophys*:85:292–95 from Brewer's yeast. This natural organic Cr compound reversed the impaired glucose tolerance of rats fed a Torula yeast based diet. (Torula yeast is usually low in chromium). Only few studies were conducted with GTF (or Brewer's yeast extracts high in GTF) on humans. Doisy, R. J. et al. In Prasad A S Oberleas D, editors. *Trace elements in human health and disease. Vol II. Essential and toxic elements*. New York: Academic Press; 1976, p 79–104 found an improvement in glucose tolerance in 50% of elderly patients with impaired glucose tolerance, after 2 months of treatment. A significant improvement in glucose tolerance and blood lipid concentration was observed in other studies after administration of Cr rich yeast extracts, Offenbacher E G, et al., 1980, *Diabetes*; 29:919–25.

In vitro studies with partially purified preparations of GTF demonstrated stimulation of glucose metabolism in several tissues in the presence of insulin. Evans G W et al, 1973, *Biochem Biophys Res Commun* 50:718–22. GTF can be extracted from several sources, including liver, black pepper, kidneys, dairy products, broccoli and barley. Anderson, R. A. and Mertz W., 1977, *Trends in Biochem. Sci.* 2, 277–279. The richest source for GTF is Brewer's yeast. Toepfer E. W. et al., 1977, *J Agric Food Chem*; 25:162–66, Mirsky N. et al., 1980, *J Inorg Biochem*, 13:11–21, 1966. In contrast to simple Cr salts that are poorly absorbed Donaldson R. M., Barreras R F. *J Lab Clin Med* 1966;68:484–93 and need a long period of treatment to achieve a partial improvement in glucose tolerance. Mertz W. *Physiol Rev* 1969;49:163–239, natural GTF exhibits remarkable improvement in glucose tolerance in both diabetic animals and human subjects Glinsmann W. H. et al., 1966, *Science*; 152:1243–45. Despite the high importance of this natural existing active Cr compound, GTF has not been characterized or identified yet.

One of the major problems related to the field of GTF, is the lability of the partially purified GTF preparations and the synthetic complexes. This lability, can partially explain the complexity of the subject, and the fact that in spite of the long time since the material was discovered, its exact composition and structure have not been determined.

The compositions of the present invention comprise two natural sources for active Chromium compounds. Brewer's yeast and Saltbush, known among the Arabs living in the Negev Desert and near the Dead Sea in Israel.

The Salt-bush (*Atriplex halimus L.*, Chenopodiaceae) is a large branched shrub, grown in arid and semi arid habitats in the Mediterranean and the Sahara-Arabian deserts. It is especially common in inundated saline depressions, and around oases of the Jordan valley. It is also commonly found in the Negev mountains, the Moav mountains and the Sinai peninsula *Flora Palaestina Part One*, PP 143–154, Michael Zohary, ed. Goldberg Press, Jerusalem, 1966.

Saltbush leaves are the exclusive source of food for the fat sand rat (Psamonys obesus; Gerbillinae), a relative large gerbillid rodent found in the Saharo-Arabian deserts Frenkel G. and Kraicer P. F., 1972, *Life Sci*. 11: 209–222; Daly M. and Daly S., 1973, *Mammalia* 37: 546–561. When fed on normal laboratory chow, or a high energy diet, sand rats develop severe hyperglycemia within 2 months Schmidt-Nielsen K & Haines H B., 1964, *Science* 143: 689–690; Hackel D B et al., 1965, Lab. Invest 14: 200–207.

Insufficient dietary Cr has been linked with diabetes Mertz W. and Schwarz K., 1959, *Am. J. Physiol.* 196: 614–618. The appearance of a cataract might be a result of several causes, among them is diabetes. The link between cataract and diabetes and low chromium and diabetes, raises the possibility that diabetic cataract is connected to low Cr concentrations in the lens. Moreover, analysis of chromium level in human lenses showed a significant reduction in chromium level in diabetic lenses when compared to normal lenses. There was no difference between senile and diabetic population. Pineau A., Guillard O. and Risse J. F., 1992, *Biol. Trace Elem. Res.* 32, 133–138.

The present invention describes the anti-diabetic effects of natural. extracts on inhibition of cataractogenesis both in vivo and in vitro.

4.5 Formulations and Dosage

Compositions containing natural and synthetic compounds, with or without chromium, of the present invention may be formulated into pharmaceutical preparations for administration to animals and humans for a variety of effects including, but not limited to, anticataract and antiretinopathy effects.

Many of the compositions containing natural and synthetic compositions with or without chromium may be provided as compounds with pharmaceutically compatible counter ions, a form in which they may be soluble.

The natural and synthetic compounds may be administered intravenously, intraperitoneally, subcutaneously, intramuscularly, intrathecally, orally, rectally, topically, or by aerosol.

Formulations suitable for oral administration include liquid solutions of the active compounds dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed contains.

Dosages for oral administration of chromium containing natural and synthetic compositions for human use range from 5 to 1000 microgram Cr/day, commonly 50 to 500 microgram Cr/day, and typically from 50 to 100 microgram Cr/day, or 0.5–50 $\mu$g Cr/Kg body weight.

Dosages for oral administration of natural and synthetic compositions for human use range from 0.05–10,000 mg/day /subject, and between 0.05%–15% w/w of the active compound formulated as eye drops.

Dosage amount and interval may be adjusted individually to provide plasma levels of the active moiety which are sufficient to maintain the antidiabetic and other favorable metabolic effects.

Alternatively, one may administer the compound in a local, rather than oral manner, for example, via injection of the compound directly into the target site, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Example of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system for example, in a liposome coated with a tissue specific antibody. The liposomes will be directed to and taken up selectively by the target issue.

In cases of local administration or selective uptake, the effective local concentration of the chromium compound may be related to plasma concentration.

The anticataract-antiretinopathy compositions of the present invention may be prepared as eye drops and exhibit an extremely strong antioxidation activity. Therefore, it is presumed that the compositions of the invention exhibit an anticataract-antiretinopathy effect by inhibiting the oxidation reaction in the lens during the process of cataractogenesis.

The compositions of the invention for the prevention or treatment of cataracts and retinopathy may be appropriately administered orally or parenterally for the prevention or treatment of those cataracts associated with oxidative disorders, such as senile cataract. In other words, the anticataract-antiretinopathy compositions of the invention exhibit a remarkable therapeutic effect not only by oral, intravenous or intraperiotoneal administration but by a direct application to the eye.

The anti-cataract-antiretinopathy compositions of the invention may be formulated into any of solid formulations such as tablets, grains, powder and capsules, and liquid formulations such as eye drops and injection solutions by known methods. These formulations may appropriately include conventionally-used excipients such as a binder, disintegrant, thickener, dispersant, reabsorption promoting agent, flavor, buffer, surfactant, resolvent, preservative, emulsifier, isotonicity inducing agent, stabilizer and pH modifier.

In the present invention, the compositions of the invention for the prevention or treatment of cataracts and retinopathy, and/or components producing different pharmaceutical effects may be combined appropriately.

In the case of the above-mentioned oral administration, the anticataract-antiretinopathy compositions of the invention may also be used as health food. Alternatively, the anticataract-antiretinopathy compositions of the invention may be added to food and drink, which may then be taken.

5. Examples

5.1 Organ Culture System (for bovine lenses).

A system for culturing eye lenses in vitro has been developed as described in U.S. Pat. No. 844944, 1987 and U.S. Pat. No. 4832486, 1989. Canadian Patents No. 479405 and No. 1236788,1988. Scanning Laser Monitor-Method and Apparatus for in Vitro Evaluation of Focal Length and Focal Length Changes in Lenses from Human and Animal Eyes). The ocular lens is an ideal organ for long-term culture experiments. Its advantages are that it has no direct blood supply and has no connection to the nervous system. This system enables maintaining lenses intact for observation and studies for periods of up to 30 days, which are appropriate for long-term experiments. It is possible in this system to monitor changes in lens optical quality. The method involves an automated scanning laser system designed to monitor focal length (spherical aberration) and transmittance of the cultured ocular lens. Focal length and scatter values for the refracted beam at each beam position and a profile of lens optical quality are produced. This is a very sensitive way to follow early damage to the eye lens. Changes in focal length can appear when the lens is still clear with no evidence of any other damage. Changes in focal length occur when lens volume is not stable (swelling). The system allows direct application to the lens of well controlled doses of glucose and approximate factors and follow the optical changes with time in culture. At different steps of the culture, lens samples are analyzed for enzymatic activities in order to understand the mechanisms by which the treatment affects the eye lens. The following enzymes present in the lens are analyzed: hexokinase (HK), aldose reductase, aldolase, glutathione reductase, glucose-6-phosphate dehydrogenase (G-6-PD), catalase and ATPase.

Organ Culture System for Bovine Lenses—materials and methods.

Bovine lenses were excised carefully from eyes obtained from animals 2 to 3 years old, 2 to 4 hours after enucleation. Each lens was placed in a specially designed culture chamber as described by Dovrat A. et al., 1986, Lens Research 3: 207–215. The culture chamber consists of two compartments connected by a round hole. The diameter of the hole is 1 mm smaller than de diameter of the lens. The lens sits between the two compartments, leaving a clear space filled with culture medium below and above the lens. Both lens surfaces were bathed in a total of 24 ml of culture medium consisting of M199 with Earle's salt, 8% fetal calf serum, and antibiotics (100 U/ml penicillin, 0.1 mg/ml streptomycin). The medium was replaced by fresh sterile medium every 24 hours. Lenses were incubated at 35° C.

5.1.1 Optical Quality Monitoring.

Lens optical quality was monitored throughout the culture period. Lens optical measurements were taken, using an automated scanning laser system that records both relative transmittance and focal length across the lens as described by Sivak J. G. et al., 1986, Vision Res. 26 (11): 1873–1879. The laser scanner consists of a low-powered helium-neon laser mounted on a computer-driven X-Y table with two video cameras and a video frame digitizer. The laser was programmed to scan across the lens in axial direction in small steps (0.5 mm), while the video cameras transmitted the image of the refracted beam to the video digitizer. A custom software program determined the focal length and relative intensity of each refracted beam from the digitizer image. The optical center was first determined for each lens by finding the position of zero, or minimum refraction, for both X and Y directions, and then the program determined the focal lengths for 11 beam positions at equal step sizes on each side of the center.

The lenses are placed in different media: control medium or high glucose medium.

Figure 1:
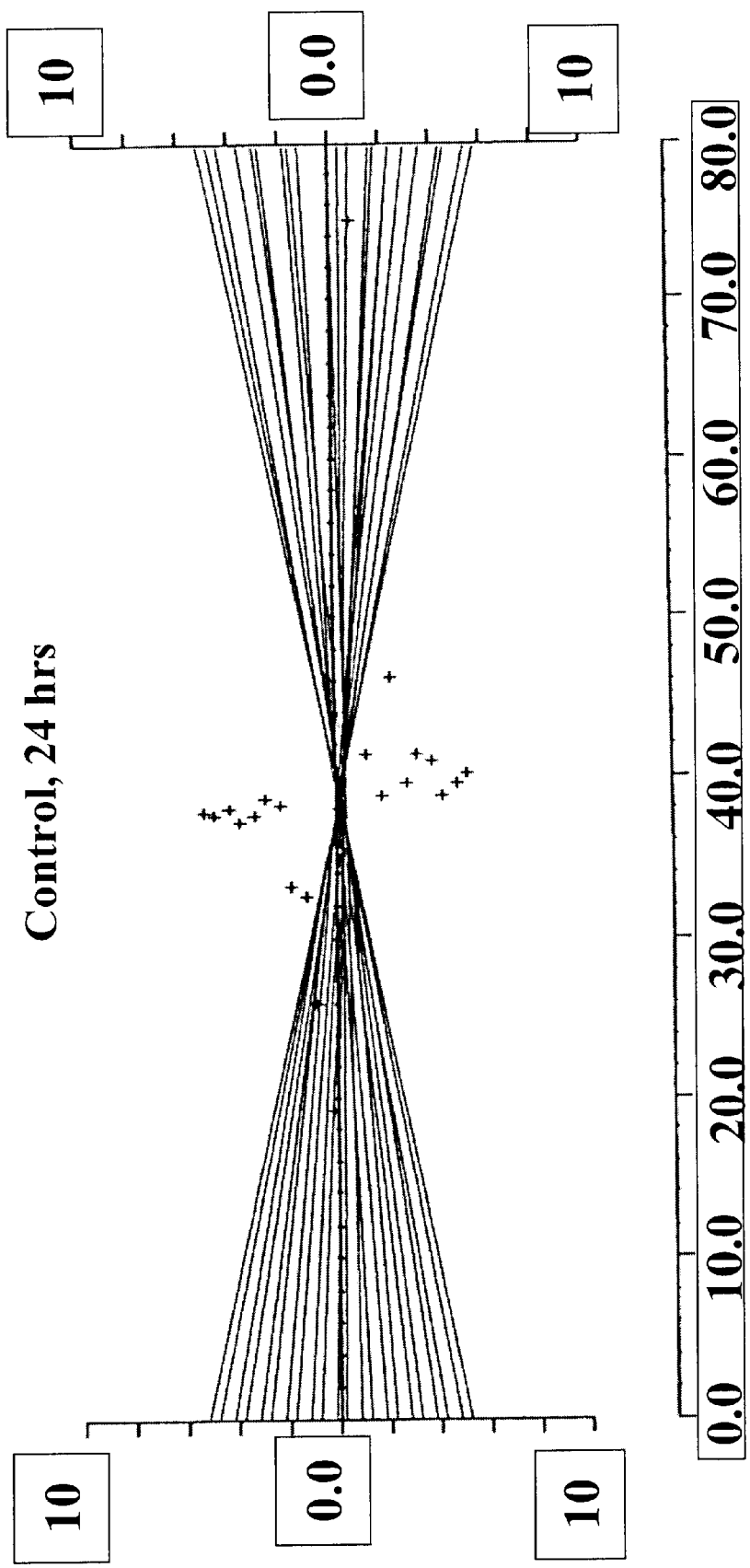
Figure 2:
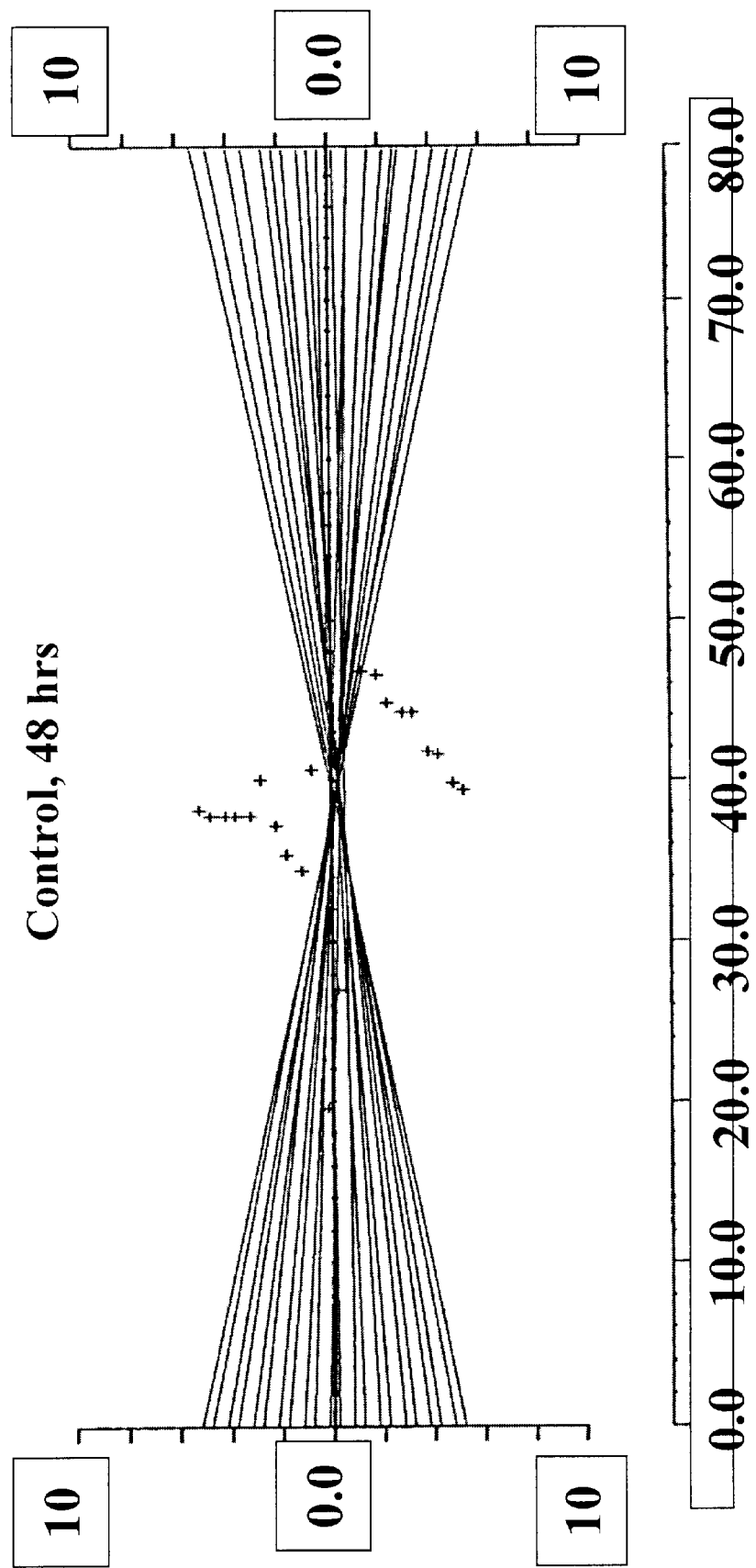
Figure 3:
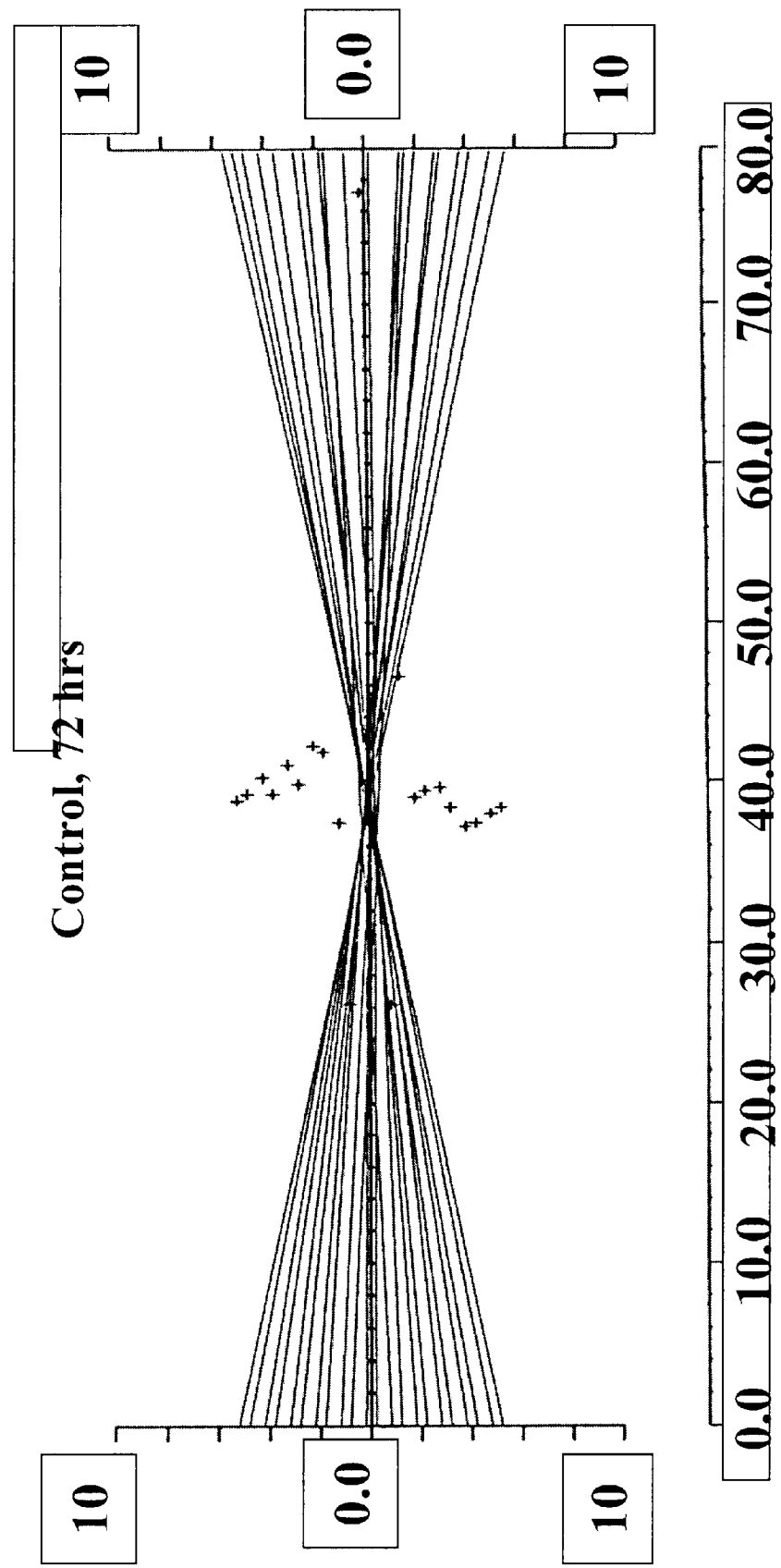
Figure 4:
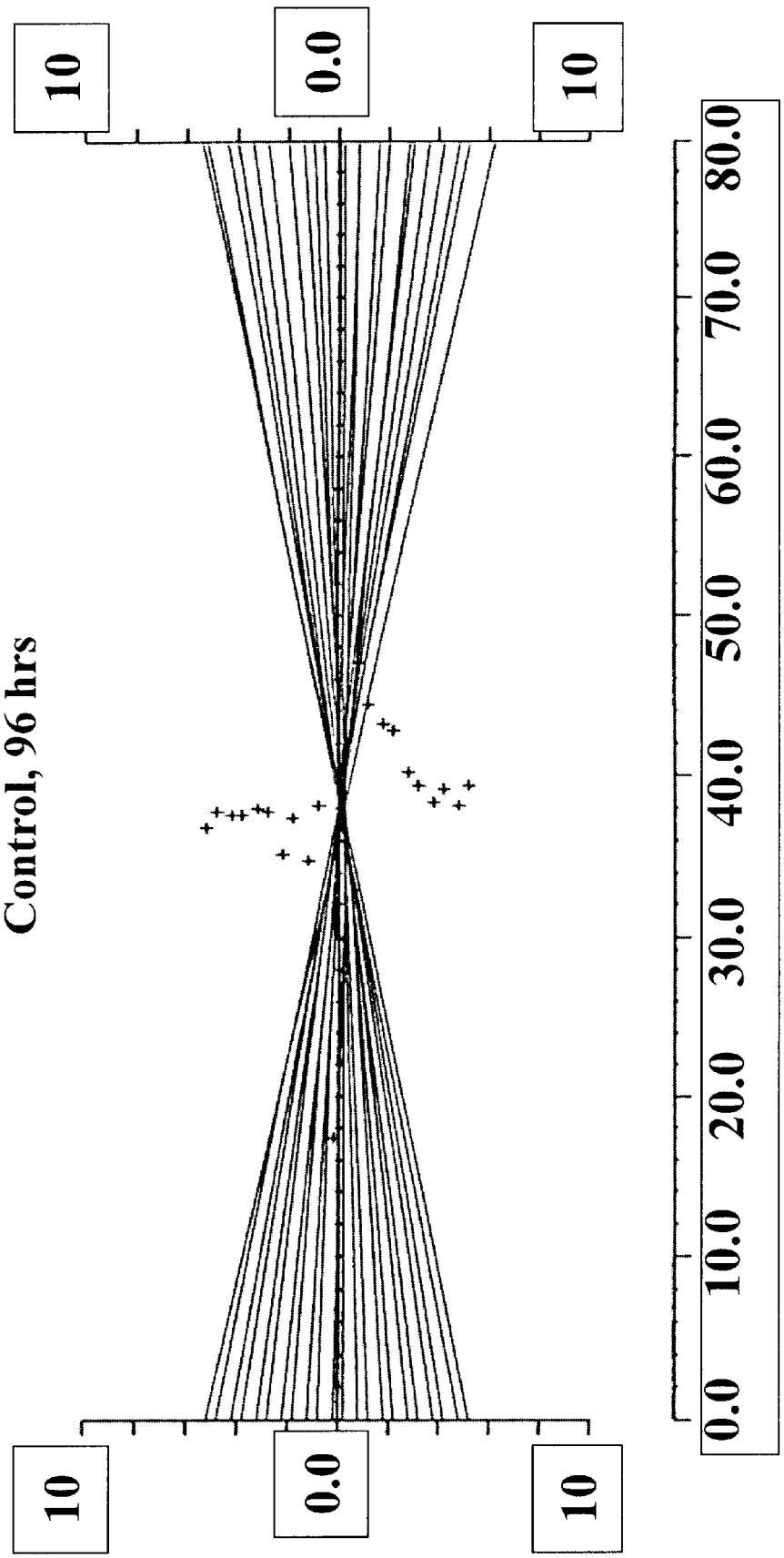
Figure 5:
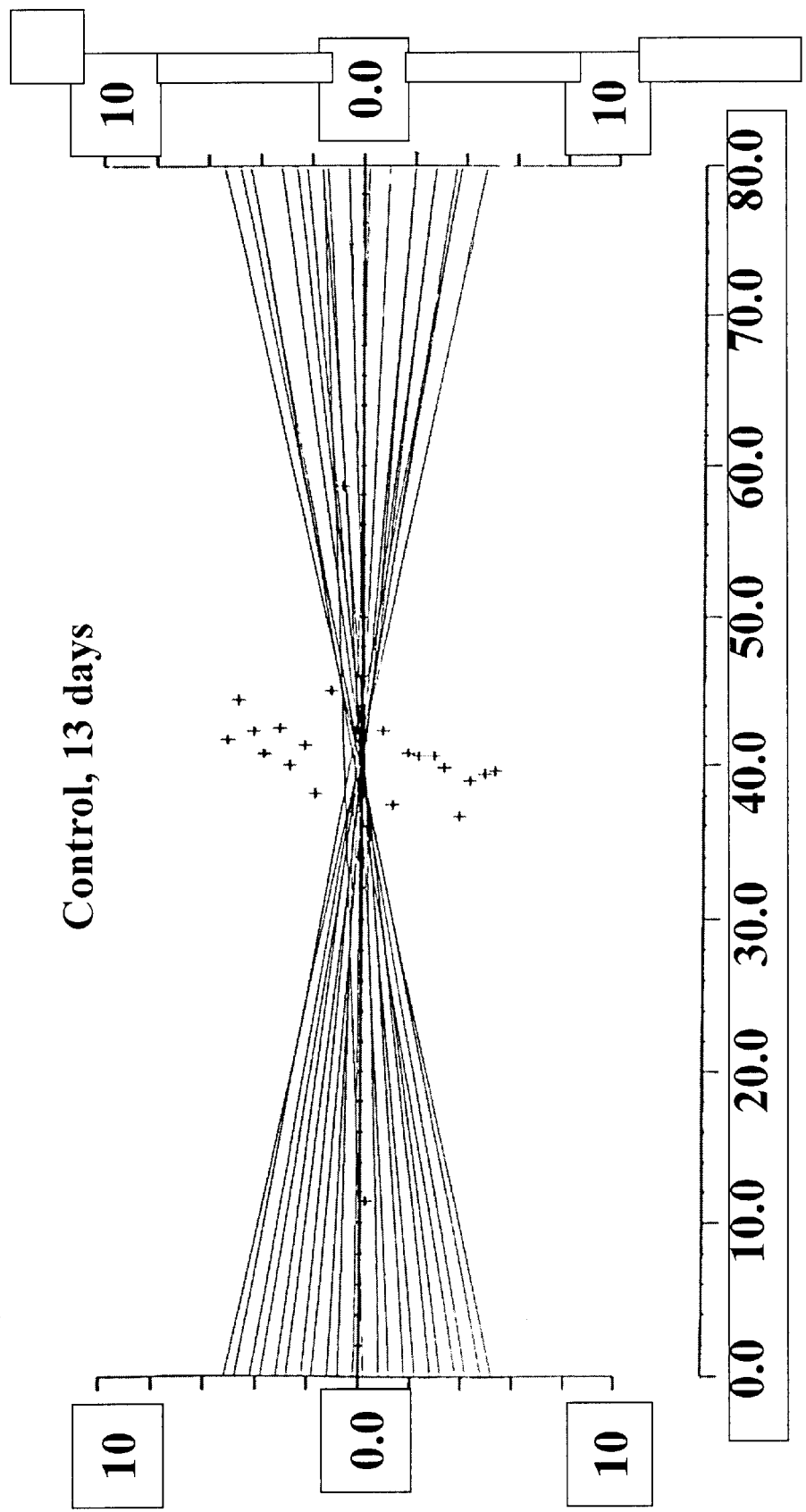
Figure 6:
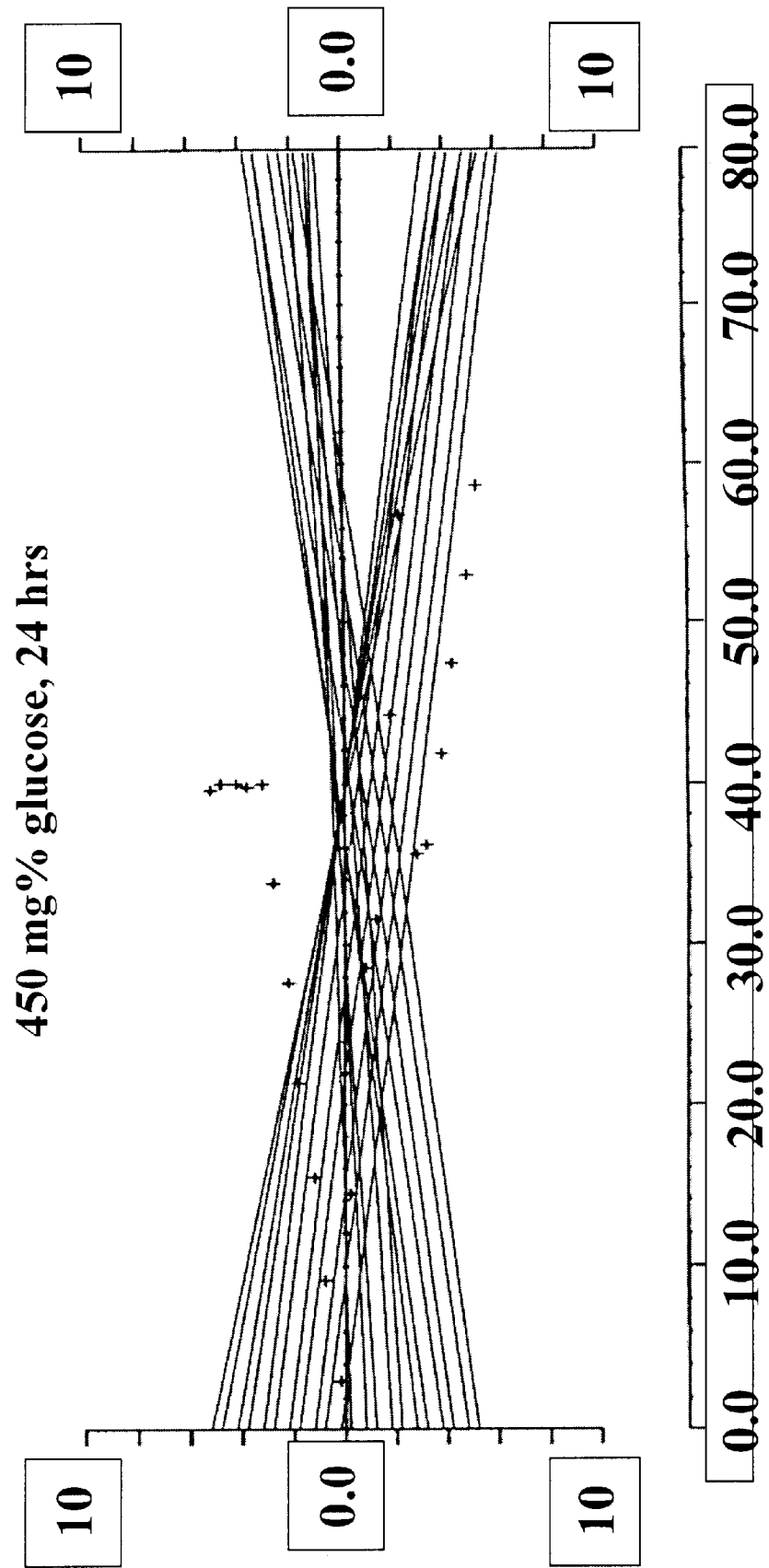
FIG. 6 is a computer printout of the Focal length profile for bovine lens, 24 hours in organ culture in the presence of 450 mg % glucose.
Figure 7:
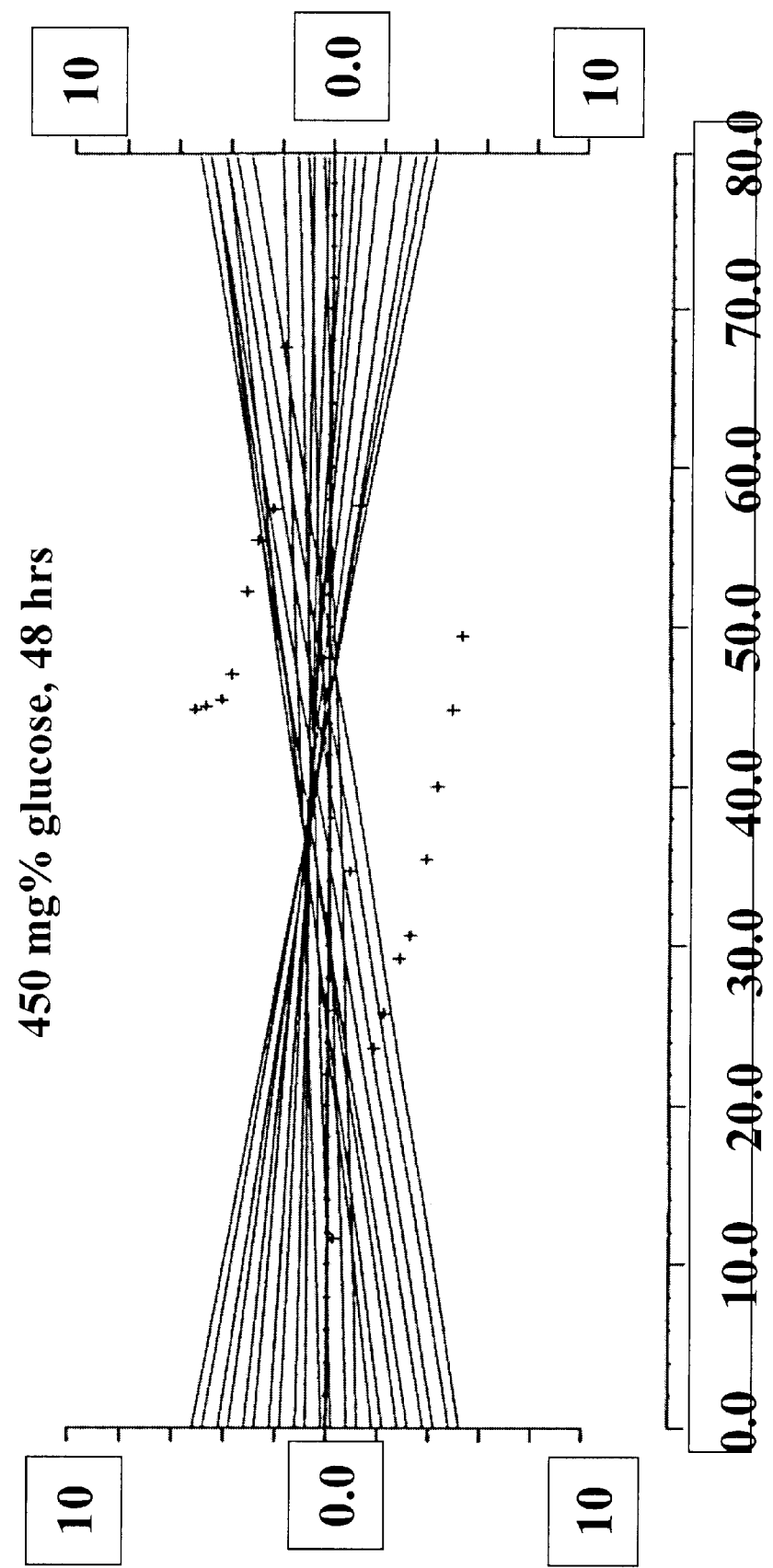
FIG. 7 is a computer printout of the Focal length profile for bovine lens, 48 hours in organ culture in the presence of 450 mg % glucose.
Figure 8:
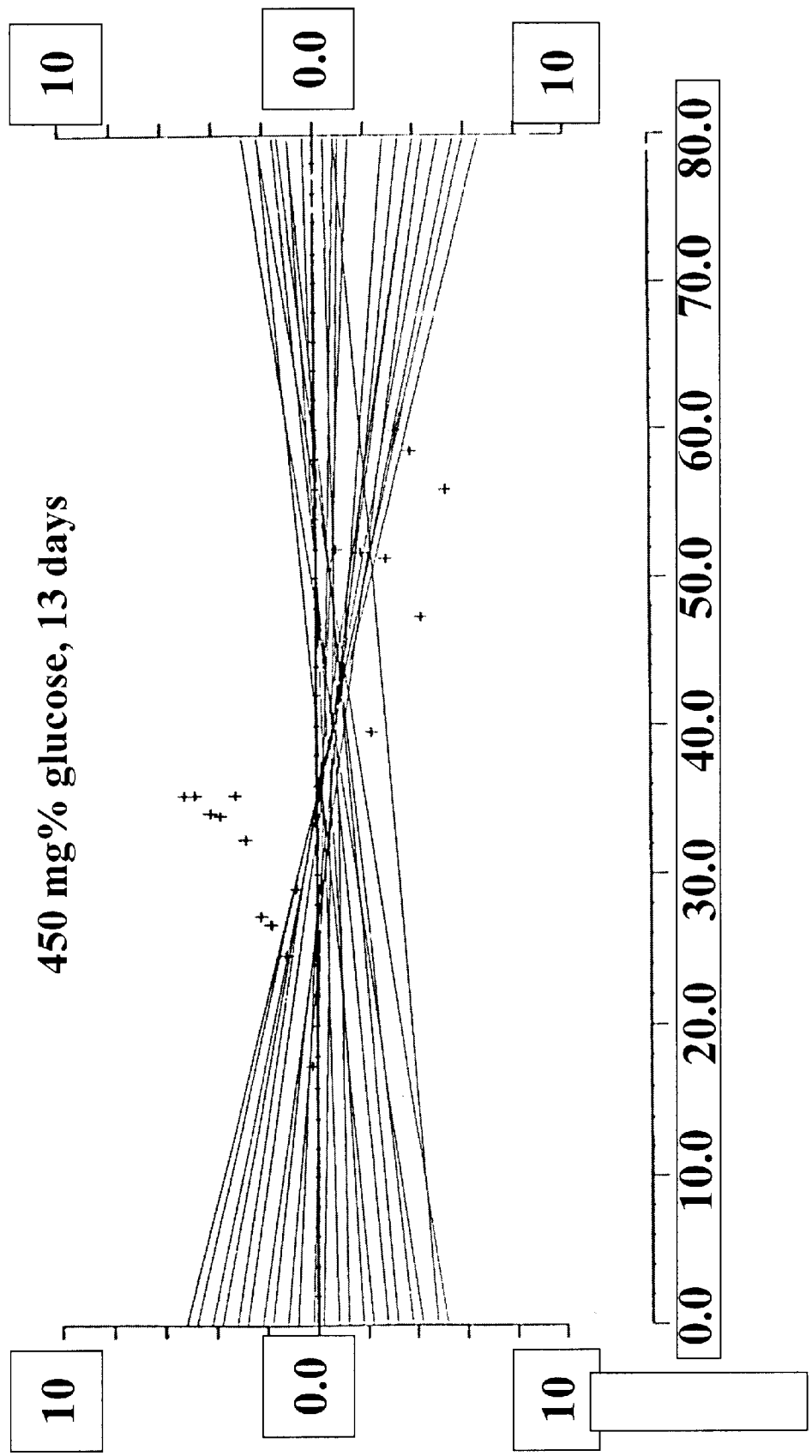
FIG. 8 is a computer printout of the Focal length profile for bovine lens, 13 days in organ culture in the presence of 450 mg % glucose.
Figure 9:
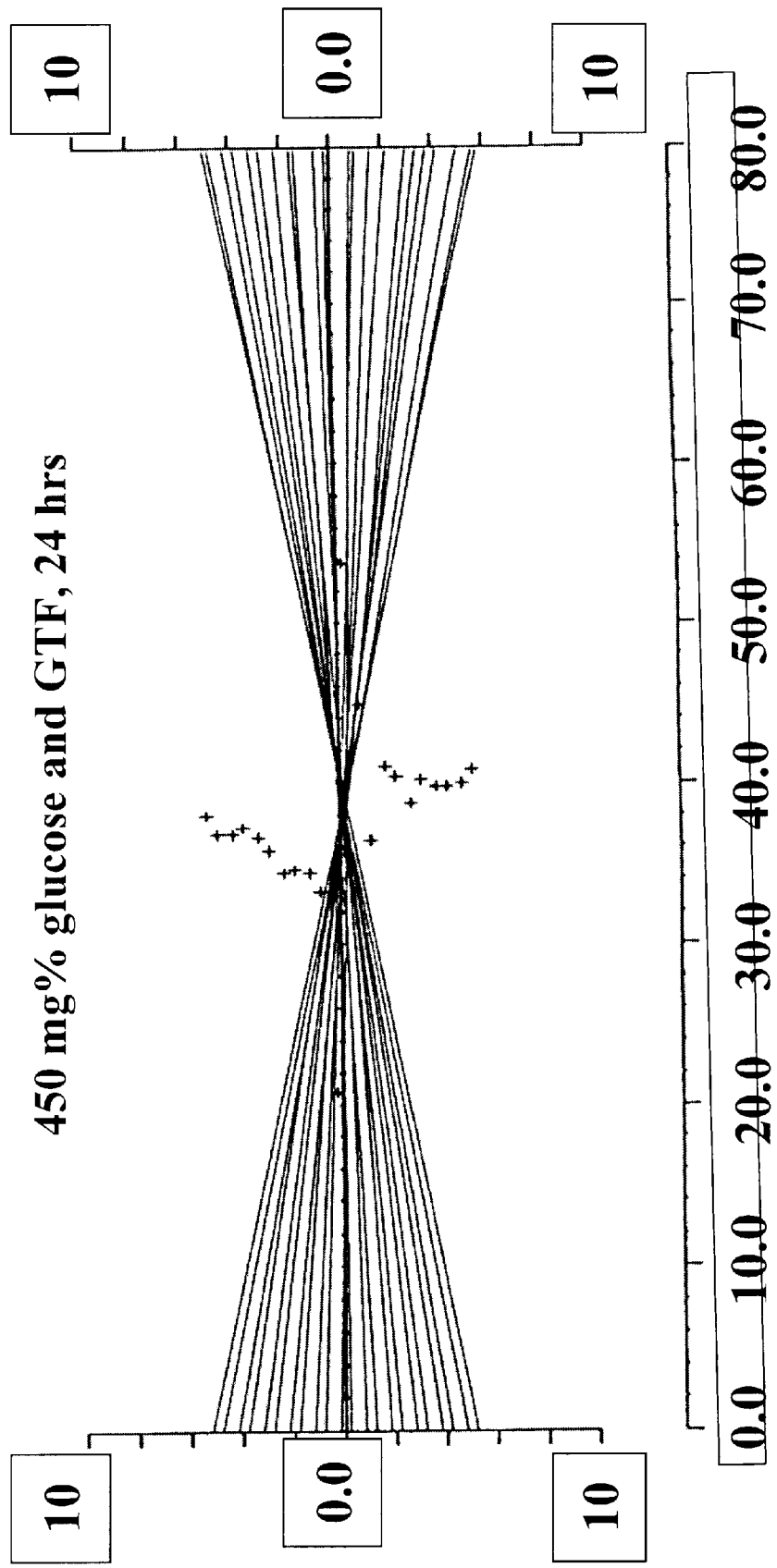
FIG. 9 is a computer printout of the Focal length profile for bovine lens, 24 hours in organ culture in the presence of 450 mg % glucose and GTF (0.167 ng Cr/ml).
Figure 10:
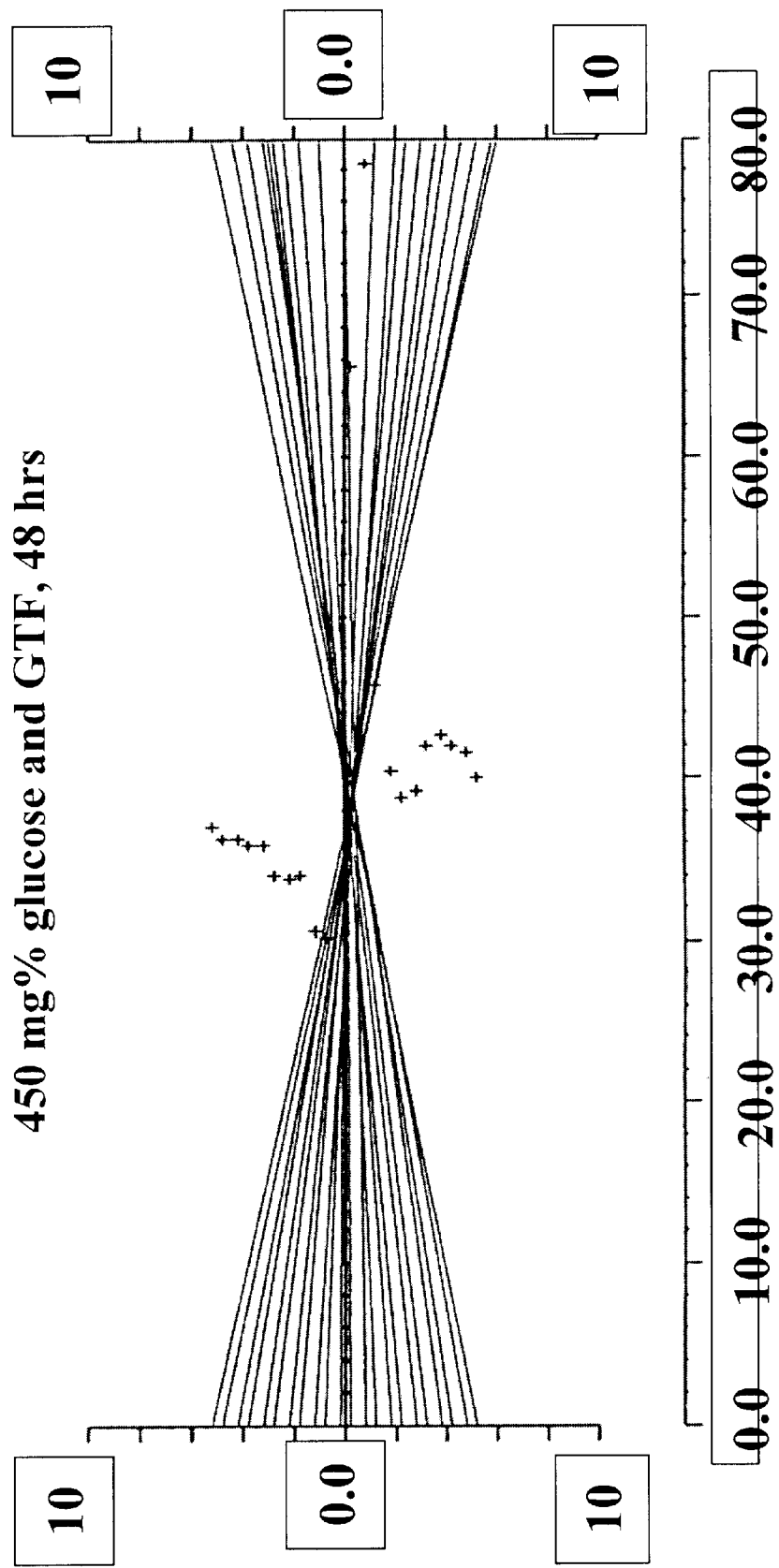
FIG. 10 is a computer printout of the Focal length profile for bovine lens, 48 hours in organ culture in the presence of 450 mg % glucose and GTF (0.167 ng Cr/ml).
Figure 11:
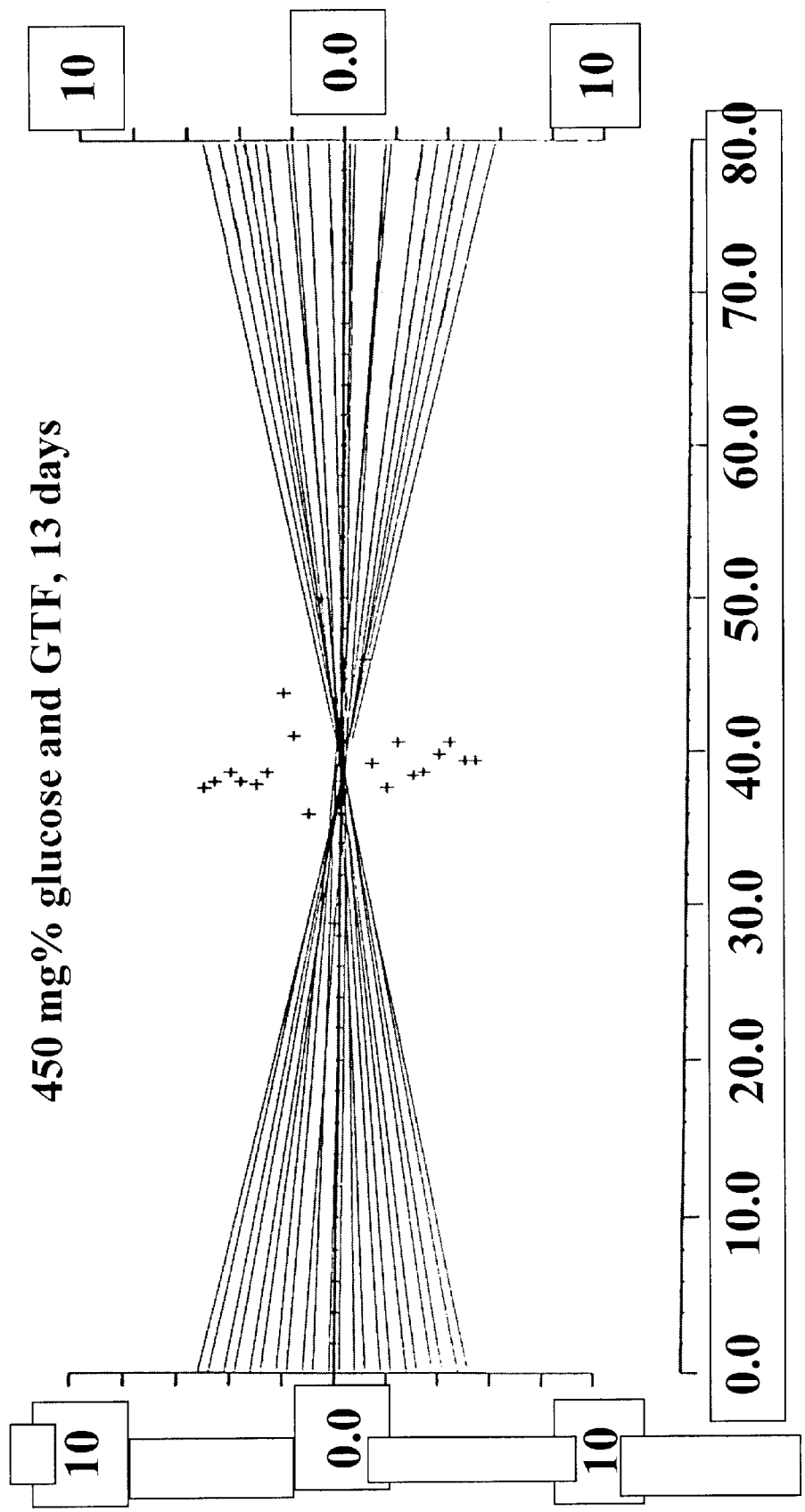
FIG. 11 is a computer printout of the Focal length profile for bovine lens, 13 days in organ culture in the presence of 450 mg % glucose and GTF.

Lenses were examined every day for two weeks and their optical quality was monitored in our automated scanning laser system. FIGS. 1–5 present focal length profiles for control lenses in organ culture monitored after 24 h, 48 h, 72 h, 96 h, and 13 days. There is no change in optical quality in the control lenses during the whole culture period. Lenses placed in high glucose medium, (450 mg % glucose), showed much higher changes in focal lens variability and a decrease in their optical quality in the same intervals monitored as shown in FIGS. 6–8. When GTF (0.167 ng Cr/ml) was added to the high glucose medium, the deleterious effects caused to the lens by high glucose were prevented, as shown in FIGS. 9–11.

5.2 Animal Experiments

Sprague Dawley male rats weighing 120–130 g were injected intraperitoneally with a single dose of streptozotocin (60 mg/kg bw) in 0.5 ml 0.05 M citrate buffer. Blood glucose levels were measured a week later, and animals with blood glucose levels above 200 mg/dl were chosen for the experiment.

Samples of GTF were prepared from yeast extract and since GTF is stable to proteolytic enzymes Mirsky et al., 1980. J. Inorg. Biochem. 13:11–21, it can be administered orally. GTF preparations were orally administered to diabetic animals by stomach tube. The oral glucose tolerance test was conducted by loading glucose (2 g/kg bw) and monitoring blood glucose at several intervals. Blood taken from the tail vein was monitored for glucose by a glucometer, One Touch II (Life Scan, CA).

Figure 12:
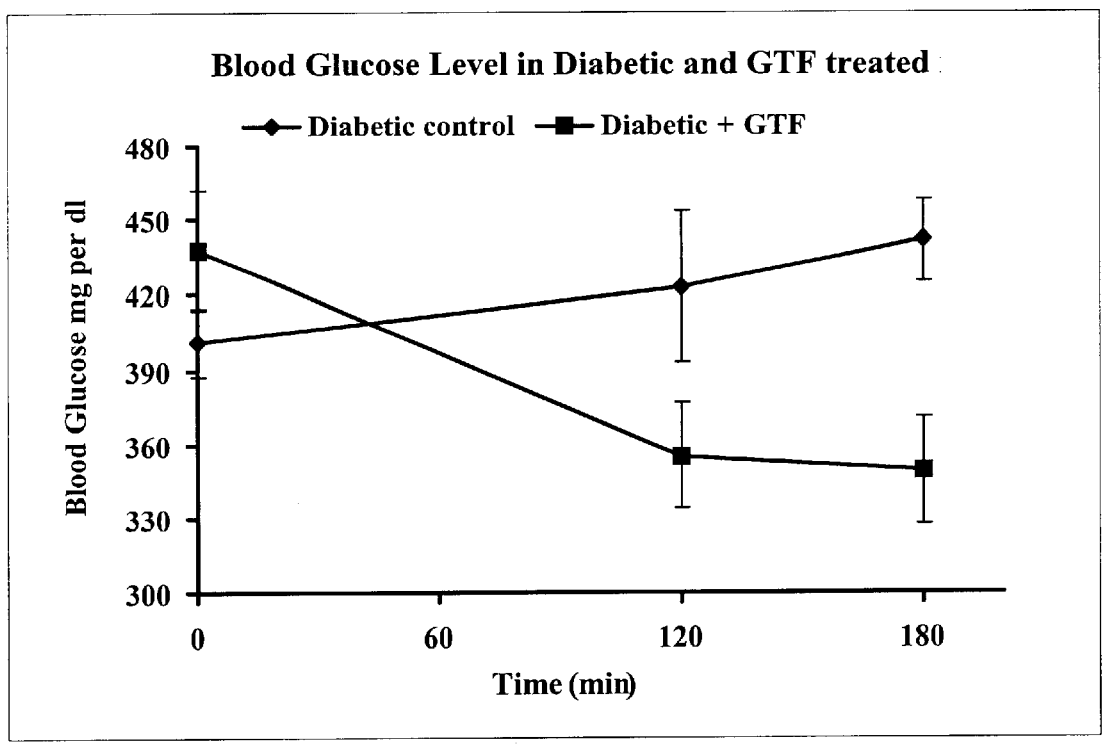
FIG. 12 illustrates the effect of a single dose of GTF (360 ng Cr/rat) on blood glucose level of diabetic rats, compared with untreated diabetic controls.

Streptozotocin diabetic rats were divided into two groups: those who were administered with a single oral dose of GTF (360 ng Cr/rat), and diabetic controls-which were left untreated. Glucose levels were measured in both groups. FIG. 12 presents a remarkable improvement in glucose levels in diabetic animals treated with GTF compared with untreated diabetic controls.

A group of diabetic animals was treated with 15 daily oral doses of GTF, another group of diabetic animals was left untreated. FIG. 13 presents the eyes of healthy animals 13(a), untreated diabetic animals, where a cataract can be distinguished 13(b), and diabetic animals treated with GTF where a remarkable inhibition in cataract formation is clearly visible (13c, 13d).

In these series of experiments SPD rats were administered with 5 oral repeated doses of GTF (560 ng Cr /dose). Rats were starved overnight prior to their sacrifice. The animals were killed by $CO_2$ and lenses were removed immediately and frozen in $-70°$ C. for enzymatic assays.

5.3 Enzymatic Assays

Lenses were removed under a binocular stereo microscope and immediately placed on ice in 0.05M phosphate buffer, pH 7.4. All additional steps were carried out at 0–4° C. The fibers attached to the lens were carefully removed. Homogenization of the lens was performed in 10 volumes of the above buffer. The homogenate was centrifuged at 14000 g for 10 minutes. Enzyme activity was measured in the supernatant. A sample of the supernatant was taken for protein determination.

Gluthathione reductase was measured according to the method of Giblin F. J. and McGready J. P., 1983, *Invest. Ophthalmol. & Vis. Sci.* 24: 113. FIG. 17 describes the results. Aldose reductase was measured according to the method of Kinoshita J. H., 1986, *Am. J. Ophthalmol.* 102:685–692. The reaction follows the formation of NADP by measuring absorbance at 340 nm.

Protein concentration of the soluble supernatant was measured by the micromethod of Lowry et al, 1951, *J. Biol. Chem.* 193: 265–275.

5.3.1 In vivo assays

Glutathione reductase (GR) is a key enzyme in the lens involved in processes of oxidation-reduction. In cases of diabetic cataracts the activity of GR is reduced. FIG. 14 presents the relative activity of GR in healthy lenses, diabetic lenses, and lenses removed from diabetic rats treated with GTF. While the activity of GR in healthy lenses is 1.16 mu/mg protein, the activity of the enzyme in control diabetic lenses is reduced to 0.72 mu/mg protein. Treatment with GTF partially recovers GR activity in the treated lenses (1.01 mu/mg protein). Aldose reductase Aldose reductase has been demonstrated to play an important role in the etiology of diabetic cataract. Its activity was found to increase in diabetic lenses when compared with control lenses. Inhibitors of aldose reductase have been reported to reduce the severity of complications in diabetic animals. Varma S. D. et al., 1975, *Science* 186: 1215. The relative activity of aldose reductase (AR) in lenses of healthy control rats, diabetic rats and diabetics treated with 5 oral doses of GTF(560 ng/Cr/dose) was measured. While AR activity in control lenses is relatively low, the enzymatic activity is much higher in diabetic untreated animals. There is a remarkable decrease in AR activity in lenses derived from animals treated with GTF as described in FIG. 15.

The inhibitory effects of the active fractions isolated from yeast, (GTF), and the saltbush, (ACMS), were examined also in vitro.

5.3.2 In vitro assays

Aldose reductase (AR) inhibition assay:

A) Preparation of crude aldose reductase from rat lenses

Rats were killed using $CO_2$ and the eyes were removed. Immediately, the lenses were excised carefully and homogenized in 2 ml of 0.1M sodium phosphate buffer (pH 6.8) in ice bath, and then centrifuged at 15000 g for 5 minutes. The supernatant was separated (crude aldose reductase (AR) fraction).

Inhibition of AR activity by fractions isolated from yeast and the saltbush:

The assay was conducted according to the procedure of Inagaki et al. (K. Inagaki, I. Miwa and T. Yashiro; J.Oku-da.Chem.Pharm.Bull; 30, 3244 (1982)) with slight modifications. The decrease in absorbance at 340 monitors the rate of NADPH oxidation by Aldose reductase.

Both GTF (derived from yeast), and ACMS (derived from the saltbush), inhibitted the activity of lens Aldose reductase by reducing the rate of NADPH oxidation as demonstrated in FIG. 16 for yeast GTF, and FIG. 17, for ACMS from the saltbush.

The overall results thus indicate that GTF alters the biochemical enzymatic actions in a favorable way to reduce cataract formation and retinopathy.

The present invention is not to be limited in scope by the embodiments disclosed in the examples which are intended as an illustration.

The present invention is not to be limited in scope by the embodiments disclosed in the examples which are intended as an illustration of one aspect of the invention any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It thus will be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

What is claimed is:

1. A method for the treatment of cataracts in a mammal, the method comprises administering to the mammal an effective amount of a composition containing natural chromium, chromium complexes or glucose tolerance factor extracts isolated from natural sources including yeast or saltbush, wherein said composition is prepared by a process comprising the steps of:

(a) mixing water extracts obtained from said natural sources with a mixture of polar organic solvents selected from the group consisting of ethanol, methanol and acetanitrile, and a non-polar organic solvent selected from the group consisting of butanol, chloroform and hexane, to produce a suspension;

(b) allowing the suspension to first separate into a non-polar phase and a polar phase, and then collecting the polar phase;

(c) subjecting the polar phase to an ethanol extraction, whereby an active eluate is collected; and (d) subjecting the active eluate from (c) to a methanol extraction to obtain an active extracted composition.

2. The method for the treatment of cataracts in a mammal according to claim 1, wherein the yeast is selected from the group consisting of *s.carlsbergenesis, s.cerevisiae, s.elipsoideus* and any commercial yeast extract.

3. The method for the treatment of cataracts in a mammal according to claim 1, further comprising an antioxidant selected from the group consisting of vitamin C, Vitamin E, reduced gluthathione, manganese, beta-carotene, ergothioneine, zinc, cysteine, N-acetyl cysteine, methionine or 2-mercapto-ethanol.

4. The method for the treatment of cataracts in a mammal according to claim 1, wherein the composition is administered orally, parentally, topically or subcutaneously.

5. The method for treatment of cataracts in a mammal according to claim 1, further comprising the steps of purifying the active extracted composition by chromatographically separating the active eluant and obtaining a fraction which has a mass spectrum comprising peaks at 86, 120, 136, 241, 288, 399, 453 and 485 m/z.

6. The method for the treatment of cataracts in a mammal according to claim 1, further comprising the steps of purifying the active extracted composition by chromatographically separating the active eluant and obtaining a fraction which has a mass spectrum comprising peaks at 104, 118, 140, 156, 186, 235, 257, 273, 315, 374 and 432 m/z.

7. The method for the treatment of cataracts in a mammal according to claim 1, further comprising the step of isolating the active composition having a molecular weight below 1000.

8. The method for the treatment of cataracts in a mammal according to claim 1, wherein said composition is administered at a daily dosage of about 0.05 to 10,000 mg of the active extracted composition.

* * * * *

UNITED STATES PATENT AND TRADEMARK OFFICE
CERTIFICATE OF CORRECTION

PATENT NO.     : 6,416,794 B1                                   Page 1 of 1
DATED          : July 9, 2002
INVENTOR(S)    : Nitsa Mirsky It is certified that error appears in the above-identified patent and that said Letters Patent is hereby corrected as shown below:

<u>Title page,</u>
Item [75], Inventor, should read:

-- [75]  Inventor: Nitsa Mirsky, Nofit (IL) and Ahuva Dovrat, Haifa (IL) --

Signed and Sealed this

Twenty-fifth Day of March, 2003

JAMES E. ROGAN
*Director of the United States Patent and Trademark Office*